United States Patent
Croizy et al.

(10) Patent No.: US 6,743,938 B1
(45) Date of Patent: Jun. 1, 2004

(54) METHOD FOR MAKING ETHYL KETONE CYANOHYDRIN

(75) Inventors: Jean-Francois Croizy, Carling (FR); Marc Esch, Freyming-Merlebach (FR); Gilbert Esquirol, Creutzwald (FR)

(73) Assignee: Atofina, Puteaux (FR)

( * ) Notice: Subject to any disclaimer, the term of this patent is extended or adjusted under 35 U.S.C. 154(b) by 0 days.

(21) Appl. No.: 10/049,463

(22) PCT Filed: Jul. 25, 2000

(86) PCT No.: PCT/FR00/02136
§ 371 (c)(1),
(2), (4) Date: Aug. 2, 2002

(87) PCT Pub. No.: WO01/09085
PCT Pub. Date: Feb. 8, 2001

(30) Foreign Application Priority Data

Jul. 29, 1999 (FR) .............................. 99 09859

(51) Int. Cl.[7] .............................. C07C 253/08
(52) U.S. Cl. ...................................... 558/351
(58) Field of Search .......................... 558/351

(56) References Cited

U.S. PATENT DOCUMENTS 4,517,132 A * 5/1985 Chan .................. 260/465

FOREIGN PATENT DOCUMENTS

| GB | 416007 | * | 9/1934 |
| GB | 452285 | * | 8/1936 |
| WO | 85 00166 | WO | 1/1985 |

OTHER PUBLICATIONS

XP002138712 Abstract—Saito, Minoru et al: "Preparation of acetone cyanohydrin" 7 pages.
XP002138711 Abstract—"Houben–Weyl Methoden Der Organischen Chemie. Band VIII" 1952, George Thieme Verleg, pp. 274–275.

* cited by examiner

Primary Examiner—Alan L. Rotman
Assistant Examiner—Ebenezer Sackey
(74) Attorney, Agent, or Firm—Millen, White, Zelano, Branigan, P.C.

(57) ABSTRACT

This process for the production of the methyl ethyl ketone cyanohydrin of formula (I) is characterized by the fact that hydrocyanic acid and methyl ethyl ketone are reacted in the presence of diethylamine as a catalyst.

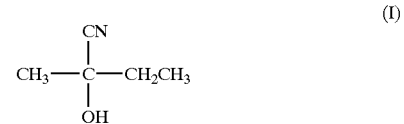

14 Claims, No Drawings

METHOD FOR MAKING ETHYL KETONE CYANOHYDRIN

This invention relates to a process for the production of the methyl ethyl ketone cynohydrin of the formula:

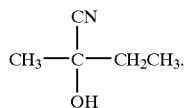

This cyanohydrin is a starting product for the production of azo polymerization triggers.

To the knowledge the filling company, the preparation of the methyl ethyl ketone cyanohydrin is not very specifically described in literature. It is possible to simply cite Example III of International Application WO 85/00166 that describes the preparation of this cyanohydrin by reaction of the methyl ethyl ketone with sodium cyanide and hydrochloric acid in water. The drawbacks of this method are the presence of water and salt in stoichiometric amounts.

According to this invention, a process is proposed to obtain the cyanohydrin in question, with fast kinetics, whereby this process is characterized by the fact that the hydrocyanic acid and the methyl ethyl ketone are reacted in the presence of diethylamine as a catalyst.

If a comparison is made with the same reaction that is conducted with the use of a solution of soda as a catalyst, an acceleration of the reaction speed is noted as a first advantage. The second advantage that can be mentioned is that, taking into account the better activity of the diethylamine relative to the soda, it is possible to use less of it, which makes it possible to limit the subsequent supply of sulfuric acid that is necessary to neutralize the catalyst before purification of the cyanohydrin (with soda, the risk of crystallization of the $Na_2SO_4$ salt is real and optionally calls for a filtration, which is not the case with a small amount of amine). It is also possible to emphasize that it is not necessary to work in the presence of traces of water that are supplied by the soda, which prevents possible segregations and limits the contents of water and hydrolysis products in the pure cyanohydrin (formic acid).

The reagents are generally initially introduced into the reactor, and diethylamine is added there while being stirred; it is also possible to add one reagent into the other in the presence of diethylamine. The reaction is balanced.

The diethylamine is preferably introduced at a rate of $10^{-3}$ to $5 \times 10^{-3}$ mol, in particular at a rate of $1.5 \times 10^{-3} - 3 \times 10^{-3}$ mol per mol of reagent too little (hydrocyanic acid or methyl ethyl ketone).

According to other characteristics of this invention, the reaction is conducted at atmospheric pressure at a temperature of $-20$ to $40°$ C., in particular from $-10$ to $30°$ C. at a pH of 7 to 9, in particular from 7.5 to 8.5, with an HCN/methyl ethyl ketone molar ratio of between 0.90 and 1.10, in particular between 0.95 and 1.05, and for a period of 1 to 4 hours, in particular from 1 to 2 hours.

The purification of the cyanohydrin that is obtained consists in neutralizing the diethylamine (for example with sulfuric acid), acidifying to no longer shift the balance and eliminating the HCN and the methyl ethyl ketone (in excess or having not reacted) by distillation under reduced pressure, by conforming to the decomposition temperature of the cyanohydrin.

The following examples illustrate this invention without, however, limiting its scope.

EXAMPLE 1 (FOR COMPARISON)

Preparation of the Methyl Ethyl Ketone Cyanohydrin With NaOH as a Catalyst

Introduced into a double-jacket reactor of 500 cm³, previously cooled to about 0° C., are about 5 mol of pure HCN at more than 99% (about 200 ml), then the equimolar amount of pure methyl ethyl ketone at more than 99% (about 400 ml) that is previously cooled.

The mixture is stirred mechanically, kept at about 0° C., then about 500 ppm (or $1.2 \times 10^{-2}$ equivalents) of NaOH is added in the form of an aqueous soda solution at 300 g/l. Up to 5 times more NaOH than provided for starting should be used, and the reaction should be continued because the soda solution is not completely miscible in the starting mixture.

The progress of the reaction based on the time is followed by taking samples (about 1 to 2 ml) and metering the HCN that has not reacted. At equilibrium, the conversion of the HCN is from 94.5–95%.

At the end of the reaction, the crude cyanohydrin is stabilized by adding sulfuric acid to neutralize the basic catalyst and to bring the pH to 2.

The thus stabilized crude cyanohydrin is topped and stripped with air for about 30 minutes in a rotary evaporator under 150 mbar (the free HCN that is recovered is trapped in the soda). The temperature is about 40° C. to limit the thermal decomposition.

880 g of methyl ethyl ketone cyanohydrin is thus obtained.

The analyses and purities that are obtained are recorded in Table 1.

EXAMPLE 2 (OF THE INVENTION)

The operating procedure of Example 1 is reproduced, except that 160 ppm of pure diethylamine (or $2.2 \times 10^{-3}$ equivalents) is used instead of the soda solution.

Thus, 950 g of the methyl ethyl ketone cyanohydrin is obtained.

The analyses and purities that are obtained are also indicated in Table 1.

TABLE 1

| Example | Purity of Methyl Ethyl Ketone Cyanohydrin (%) (1) | Water (%) (2) | Free HCN (%) (3) | Methyl Ethyl Ketone + Impurities (%) (4) | $H_2SO_4$ (ppm) (5) |
|---|---|---|---|---|---|
| 1 (For Comparison) | 96.74 | 0.50 | 0.27 | 2.49 | 1750 |
| 2 (Of the Invention) | 98.18 | 0.21 | 0.49 | 1.12 | 850 |

(1) Total HCN metering (Deniges)
(2) Karl Fischer (water that is obtained from the HCN or methyl ethyl ketone reagents and primarily from the soda in Example 1)
(3) Charpentier-Volhard metering
(4) Addition to 100%
(5) Acidimetry

What is claimed is:

1. A process for the production of methyl ethyl ketone cyanohydrin of the formula:

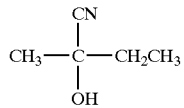

said process comprising:
reacting hydrocyanic acid and methyl ethyl ketone in the presence of diethylamine as a catalyst.

2. A process according to claim 1, wherein the diethylamine is introduced at a rate of $1 \times 10^{-3}$ to $5 \times 10^{-3}$ mol per mol of hydrocyanic acid or methyl ethyl ketone, whichever is in the lowest molar concentration.

3. A process according to claim 2, wherein the diethylamine is introduced at a rate of $1.5 \times 10^{-3}$ to $3 \times 10^{-3}$ mol per mol of hydrocyanic acid or methyl ethyl ketone, whichever is in the lowest molar concentration.

4. A process according to claim 1, wherein the reaction is conducted at atmospheric pressure.

5. A process according to claim 1, wherein the reaction is conducted at a temperature of −20 to 40° C.

6. A process according to claim 5, wherein the reaction is conducted at a temperature of −10 to 30° C.

7. A process according to claim 1, wherein the reaction is conducted at a pH from 7 to 9.

8. A process according to claim 7, wherein the reaction is conducted at a pH of 7.5 to 8.5.

9. A process according to claim 1, wherein the reaction is conducted with an HCN/methyl ethyl ketone molar ratio of between 0.90 and 1.10.

10. A process according to claim 1, wherein the reaction is conducted for a period of 1 to 4 hours.

11. A process according to claim 9, wherein the reaction is conducted with an HCN/methyl ethyl ketone molar ratio of between 0.95 and 1.05.

12. A process according to claim 10, wherein the reaction is conducted for a period of 1 to 2 hours.

13. A process according to claim 2, wherein the reaction is conducted at a temperature of −20 to 40° C., a pH from 7 to 9, and at an HCN/methyl ethyl ketone molar ratio of between 0.90 and 1.10.

14. A process according to claim 3, wherein the reaction is conducted at a temperature of −10 to 30° C., a pH from 7.5 to 8.5, and at an HCN/methyl ethyl ketone molar ratio of between 0.95 and 1.05.

* * * * *